United States Patent [19]

Lee et al.

[11] Patent Number: 4,658,208
[45] Date of Patent: Apr. 14, 1987

[54] DOWNHOLE STEAM QUALITY MEASUREMENT

[75] Inventors: David O. Lee; Paul C. Montoya; James F. Muir; J. Robert Wayland, Jr., all of Albuquerque, N. Mex.

[73] Assignee: The United States of America as represented by the United States Department of Energy, Washington, D.C.

[21] Appl. No.: 746,593

[22] Filed: Jun. 19, 1985

[51] Int. Cl.⁴ .............................................. G01N 15/00
[52] U.S. Cl. .................................. 324/61 R; 324/453; 73/61 R
[58] Field of Search ................... 73/61 R, 29; 175/40; 324/65 P, 65 R, 61 P, 61 R, 453; 374/42

[56] References Cited

U.S. PATENT DOCUMENTS

| | | |
|---|---|---|
| 2,146,312 | 2/1939 | Powell . |
| 2,542,944 | 2/1951 | Rieber . |
| 2,979,950 | 4/1961 | Leone . |
| 3,083,565 | 4/1963 | Jennings . |
| 3,284,003 | 11/1966 | Ciemochowski . |
| 3,416,356 | 12/1968 | Bridgeman . |
| 3,424,977 | 1/1969 | Krobath ............................ 324/61 P |
| 3,552,186 | 1/1971 | Sproul . |
| 3,721,121 | 3/1973 | Fierfort ............................. 73/61 R |
| 3,780,564 | 12/1973 | Levina . |
| 3,937,059 | 2/1976 | Nisolle . |
| 4,281,286 | 7/1981 | Briggs ............................. 324/61 R |
| 4,288,741 | 9/1981 | Dechene ........................... 324/61 R |

FOREIGN PATENT DOCUMENTS 0169049  10/1983  Japan ................................. 73/61 R

OTHER PUBLICATIONS

Wayland: "Measurement of Resistivity Changes Induced by In situ Combustion", Sandia Report–SAND-82–0874–Jul. 1982.

Primary Examiner—Reinhard J. Eisenzopf
Assistant Examiner—Jose M. Solis
Attorney, Agent, or Firm—George H. Libman; Albert Sopp; Judson R. Hightower

[57] ABSTRACT

An empirical method for the remote sensing of steam quality that can be easily adapted to downhole steam quality measurements by measuring the electrical properties of two-phase flow across electrode grids at low frequencies.

8 Claims, 9 Drawing Figures

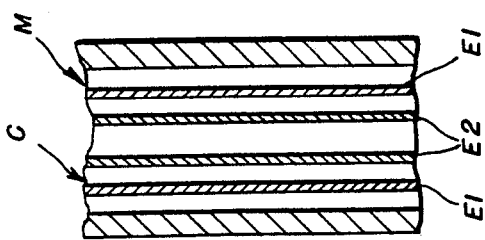
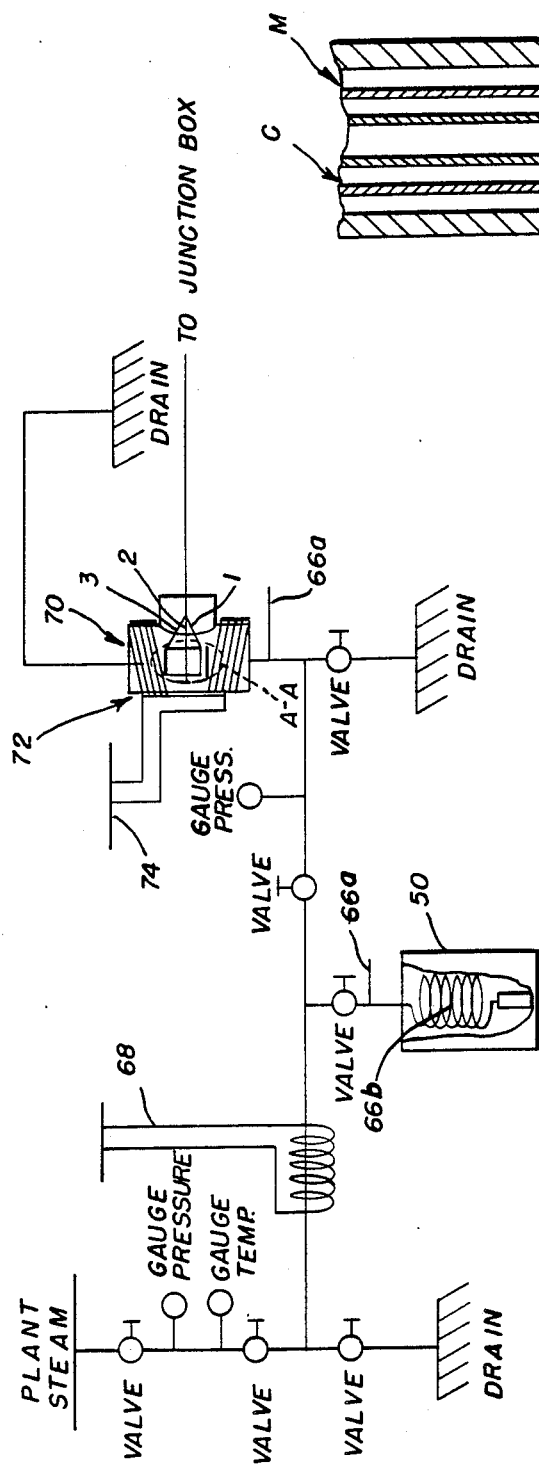
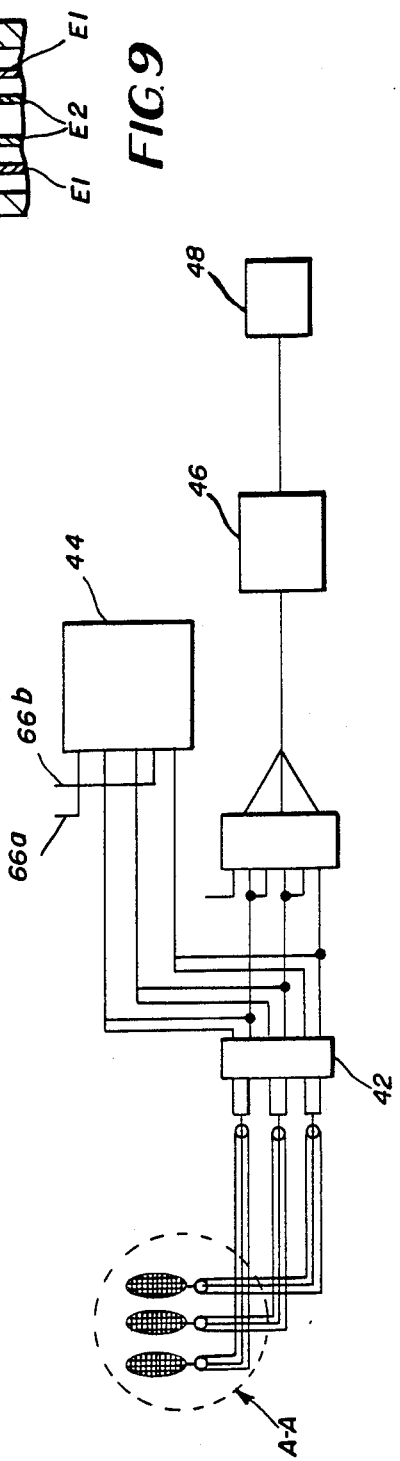

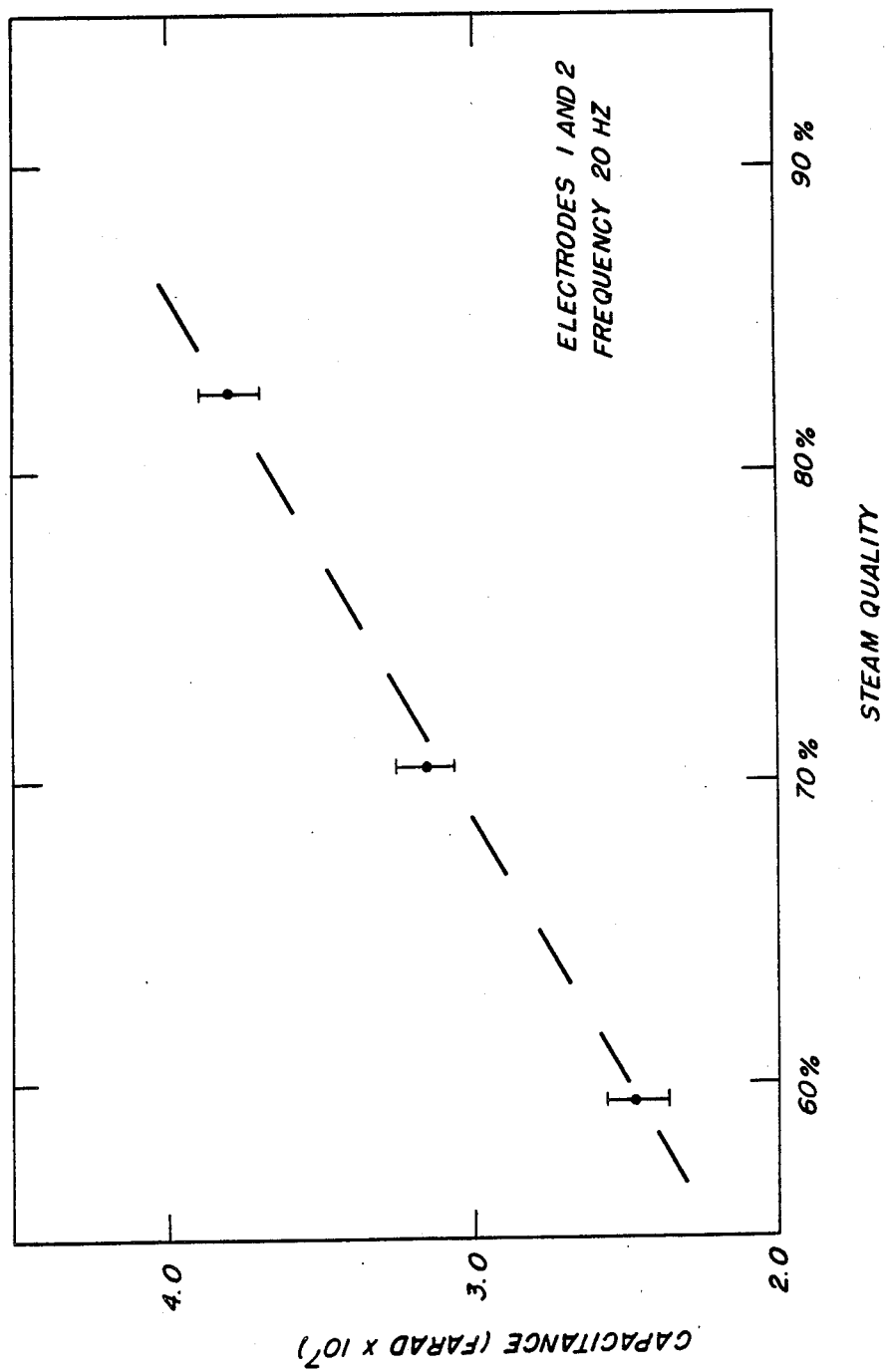

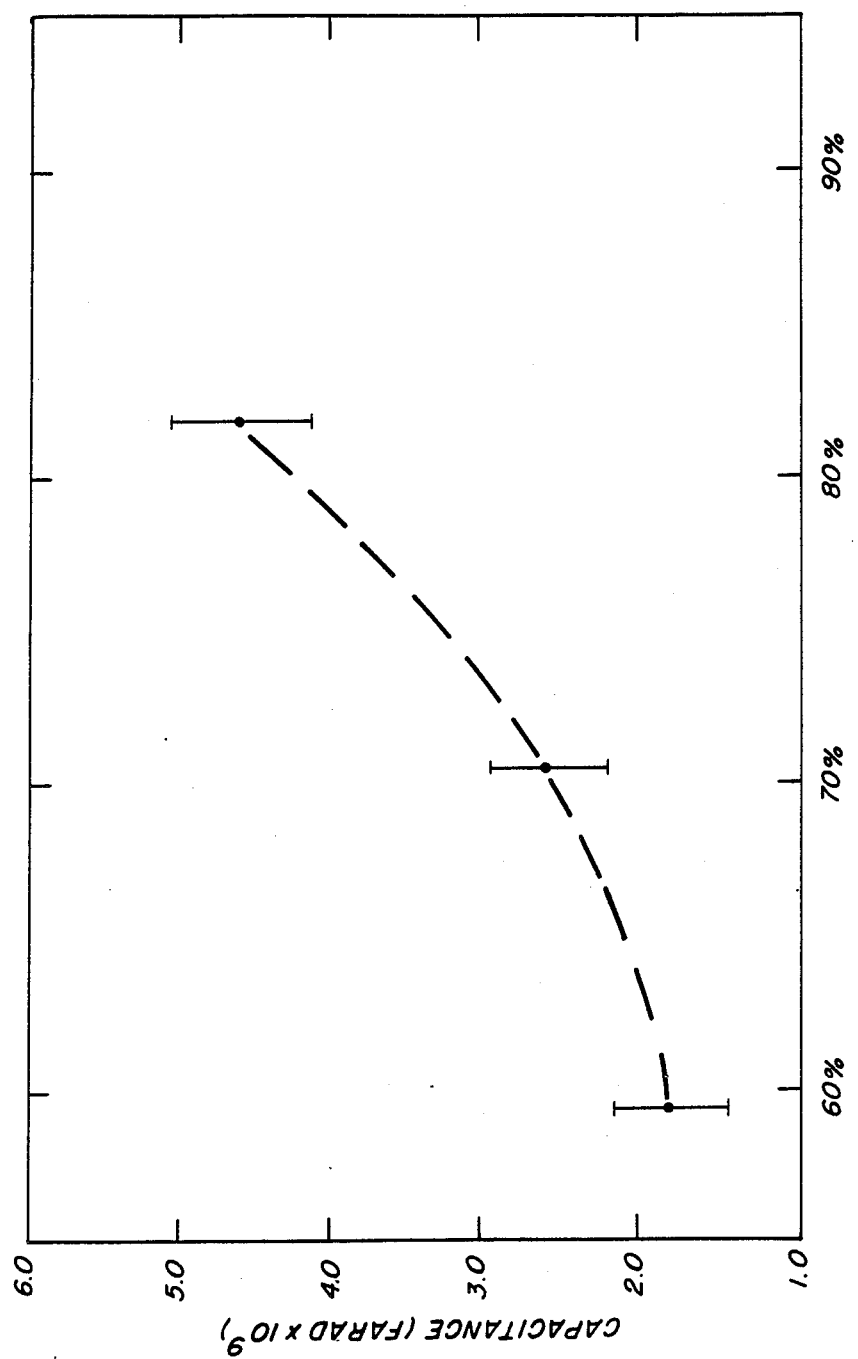

DOWNHOLE STEAM QUALITY MEASUREMENT

The United States Government has rights in this invention pursuant to Contract No. DE-AC04-76DP00789 between the Department of Energy and AT&T Technologies, Inc.

BACKGROUND OF THE INVENTION

The present invention relates to an empirical electrical method for remote sensing of steam quality utilizing flow-through grids which allow measurement of the electrical properties of a flowing two-phase mixture.

The measurement of steam quality in the oil field is important to the efficient application of steam assisted recovery of oil. Because of the increased energy content in higher quality steam it is important to maintain the highest possible steam quality at the injection sandface. The effectiveness of a steaming operation without a measure of steam quality downhole close to the point of injection would be difficult to determine. Therefore, a need exists for the remote sensing of steam quality.

A number of methods currently exist for the measurement of steam quality. For example, a December 1981 publication by Sandia National Laboratories, SAND80-7134, contains an article by A. R. Shouman entitled "Steam Quality Measurement: A State of the Art Review". Shouman reviewed existing methods and identified two techniques which could be useful for remote sensing of pure steam, one based on acoustic propagation characteristics of two-phase flow and a second on venturimeters.

Another method is disclosed by H. A. Wong, D.S. Scott, and E. Rhodes in an article "Flow Metering in Horizontal Adiabatic Two-Phase Flows" found in *Flow/81: Its Measurement and Control in Science and Industry*, Vol. 2, 1981, pp. 505-516. Wong et al. have developed a twisted tape venturimeter for two-phase quality measurements. Although this method has been used for steam quality measurements in the field, no detailed calibration measurements on wet, high pressure steam have been reported.

A venturimeter/orifice plate system has been used successfully (although not downhole) for wet steam quality measurements at up to 980 pounds per square inch (psi) by D. B. Collins and M. Gacesa as described in the March 1971 publication of *J. Basic Engineering* on pp. 11-21.

Other more recent techniques of steam quality measurement include gamma and x-ray attenuation. In order to be useful however, they require extensive calibration against known standards over the complete range of conditions which may be encountered downhole.

Therefore it is desired to provide an empirical electrical method for the remote sensing of steam quality that can be adapted to downhole steam quality measurement.

SUMMARY OF THE INVENTION

Accordingly, it is an object of the present invention to provide an empirical method for the remote sensing of steam quality.

It is another object of the present invention to provide an empirical method for the remote sensing of steam quality that can be easily adapted to downhole steam quality measurements.

It is a further object of the present invention to provide a device for allowing measurement of the electrical properties of two-phase flow in the method of steam quality measurement.

It is a still further object of the present invention to provide a device for allowing measurement of the electrical properties of two-phase flow in the method of steam quality measurement which will not alter the flow characteristics and at the same time be able to withstand an adverse environment.

Briefly described, in accordance with the present invention, an empirical electrical method for the remote sensing of steam quality has been developed. A device is made from special flow-through grids which allow measurement of the electrical properties of a flowing two-phase mixture without interfering with the flow. The effect on the capacitance of the flowing mixture at low frequencies yield a straight line relationship. The device must be calibrated for each specific application, and clearly can be adapted to other applications.

More specifically, the present invention is directed to a method for measuring the quality of steam flowing through a conduit in a downhole oil well system at the injection sandface, the improvement comprising the steps of: calibrating the system by filling a conduit containing two spaced electrodes with steam samples of known qualities; applying an AC signal across the terminals; measuring the capacitance between the electrodes as a function of frequency of the applied signal for each steam sample; and determining a frequency range where measured capacitance is a linear function of steam quality. The calibrated system is then used by injecting an unknown sample of steam into the conduit; applying an AC signal at a selected frequency within the frequency range to the electrodes; measuring the capacitance between the electrodes at the selected frequency; and determining steam quality from the capacitance measurement.

The electrodes may be spaced either longitudinally of the conduit in which case planar electrodes are used or transversely of the conduit in which case cylindrical electrodes are used.

In either case the electrodes are disposed downhole adjacent to the oil well sandface and all capacitance measurements are made remotely above the steam injection zone.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 4 is a diagrammatic view of the laboratory apparatus utilized for measuring steam quality with the standard calorimeter techniques of the enthalpy tank of FIG. 3 and the electrical properties using the electrodes of FIG. 2 for developing the empirical data to be utilized in the downhole steam quality measurement method of the present invention;

FIG. 5 is a diagrammatic view of a data analyzing and recording system for the steam quality and electrical parameters measured by the system of FIG. 4;

FIG. 6 is a graph showing a correlation of steam quality with the measured capacitance between a pair of electrodes of FIG. 2 having capacitance at a low frequency voltage signal (20 Hz) applied therebetween;

FIG. 7 is a graph showing a correlation of steam quality with the measured capacitance between a pair of electrodes of FIG. 2 with a high frequency voltage signal (2000 Hz) applied therebetween;

FIG. 9 is an alternative embodiment of cylindrical electrodes spaced transversely of a conduit through which steam is flowing at a downhole location.

DETAILED DESCRIPTION OF THE INVENTION

Figure 1:
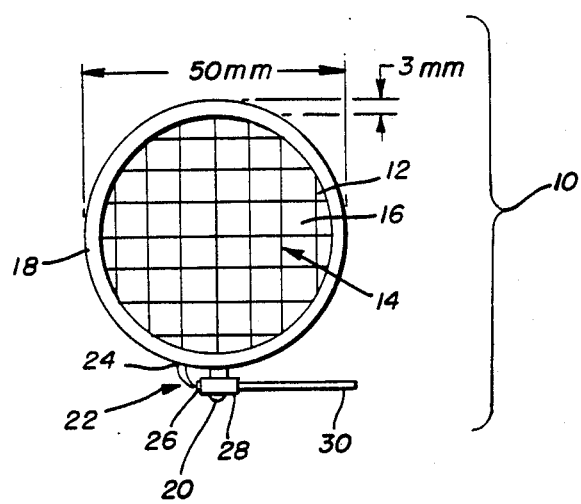
FIG. 1 is a plan view of a single planar flow-through electrode a pair of which are utilized to measure the steam quality in accordance with the present invention.

Referring in detail to FIG. 1 there is illustrated a single flow-through electrode 10 for measurement of electrical and thermal properties of steam flowing therethrough. As will become more readily apparent hereinafter a spaced pair of such electrodes will be utilized in accordance with the present invention to measure steam quality downhole near the sandface of an oil well.

Each electrode 10 is made using a computer-generated rectangular grid pattern 12 of 0.51 mm wires 14 on a 6 mm grid space 16 surrounded by a 25 mm outer annulus 18 of a 3 mm width. A tab 20 extends from the outer annulus 18. This computer-generated pattern is photo etched onto 0.13 mm 304 stainless steel resulting in a physical electrode having parts corresponding to those computer-generated parts described hereinabove.

Electrodes 10 are plated with Wood's nickel strike to a thickness of about 0.0025 to 0.005 mm and then with about 0.0025 to 0.0037 mm of gold on top of the nickel by the Englehart technique. Electrical connection to the electrode 10 is made with 2.18 mm chromel/alumel, stainless steel sheath thermocouple wires 22 with the ball spot welded to the electrode 10 at a point 24. The sheath 22 is sealed with RE-X glass ceramic 26 at one end of a bidirectional sleeve 28 mounted in a perpendicular arrangement on tab 20.

The RE-X glass ceramic 26 was developed by General Electric for high voltage insulators and has a coefficient of expansion closely matched to chromel/alumel resulting in a good glass to metal seal. RE-X glass ceramic 26 is workable at 950° C. but will withstand a continuous temperature of 830° C. without degradation rendering it highly suitable for application in downhole steam measurement. This glass ceramic 26 has a weathering resistance better than glass and as good as glazed porcelain.

At the sleeve 28 end opposite that of the ceramic seal 26 are electrode leads 30 to be coupled to an impedance analyzer and thermocouple readout provided in the data recording system of FIG. 5 to be described hereinafter.

Figure 2:
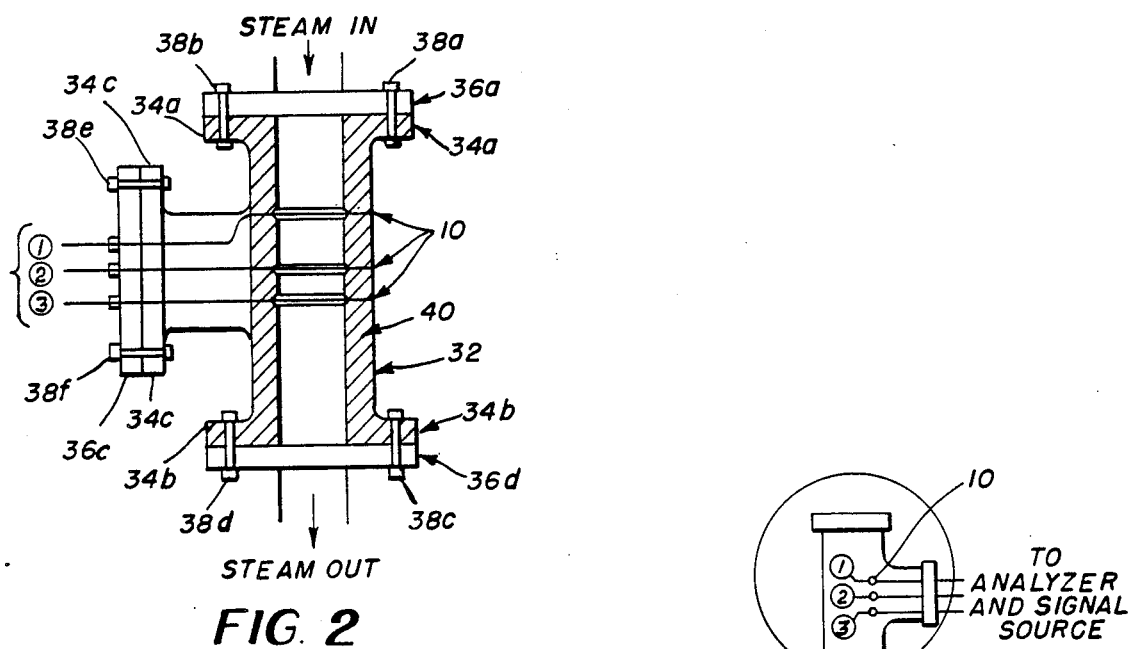
FIG. 2 is a side elevational view partially in section illustrating three flow-through electrodes of the type illustrated in FIG. 1 mounted in a pipe for measurement of electrical and thermal properties of steam flowing therethrough.

Referring to FIG. 2 there is illustrated a side elevational view partially in section of an electrical grid system of a plurality of spaced flow-through electrodes 10 for measurement of electrical and thermal properties of steam flowing through a conduit or tube 32. The tube 32 is disposed in the laboratory system of FIG. 4 to be described hereinafter.

Three electrodes 10 are mounted in a 50 mm ID pyrex T-tube 32 having flanged ends 34a, b and c with gaskets 36a, b and c mounted to each respective flanged end 34a, b and c by any suitable attachment means such as bolts 38(a-f). The three electrodes 10 are held in place by phenolic (laminated sheet cloth fabric base) spacers 40 with a 50 mm outer diameter and a 25 mm inner diameter. These spacers 40 are arranged such that the distance between each adjacent electrode 10 is 12 mm.

Leads 30 from the electrodes 10 and thermocouples 22 are fed out through the right angle section of the pyrex T-tube 32 to a junction box 42 (see FIG. 4). The junction box 42 serves as the branching off area whereby it is possible to measure either temperature through the thermocouples 22 of each electrode 10 or electrical parameters through just one lead 30 of each thermocouple 22. Use of this junction box 42 is useful to prevent interference between temperature measurements and measurements of electrical parameters.

Figure 3:
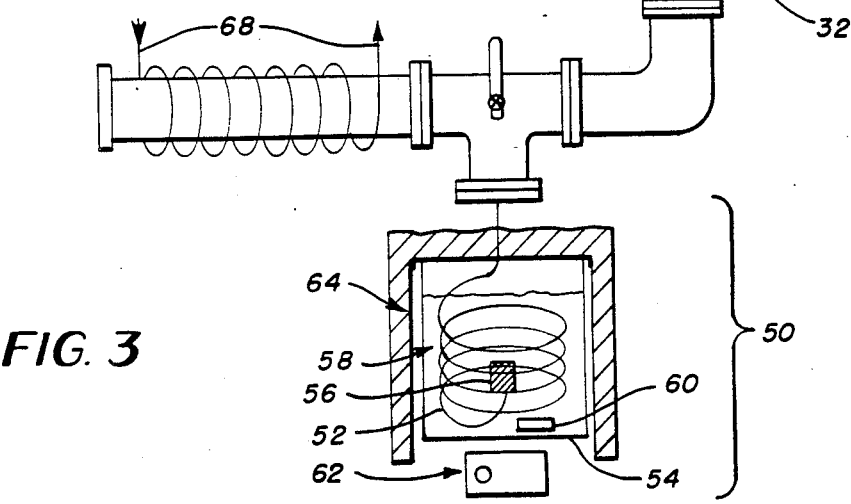
FIG. 3 is a diagrammatic view of a portion of a flow system including a cooler bath, a conventional enthalpy tank for measuring steam quality, and an input to an analyzer and signal source.

FIG. 3 illustrates a portion of a flow system including conventional enthalpy tank 50 utilized in the laboratory system of FIG. 4 to be described hereinafter for measuring steam quality using standard condensing calorimeter techniques.

An enthalpy tank 50 is made by forming a coil 52 of 10 mm copper inside a container 54. Steam is passed through the coil 52 and allowed to exit through a perforated cylinder 56 at the end of the coil 52 and into water 58. The initial column of water 58 should be chosen to cover both the coil 52 and exit cylinder 56. A stirring magnet 60 located on the bottom of the enthalpy tank 50 is activated by a stirrer motor 62 and subsequently keeps the water 58 well mixed.

A small change in temperature ($\Delta T$) of the water is used to measure the initial and final mass and temperature of the water over a range of 30° C. in order to reduce evaporative losses as much as possible. The container 54 is insulated by insulation blanket 64 to minimize heat loss and thermal variations.

The actual calculation of steam quality X is a result of the equation:

$$X = \frac{h - h_f}{h_{fg}}$$

where $h_f$ is the enthalpy of saturated liquid, $h_{fg}$ is the change in enthalpy between a saturated liquid and a saturated vapor, and h is the measured enthalpy. Values for $h_f$ and $h_{fg}$ are taken from standard tables for the measured values of the steam temperature and/or pressure.

All measured quantities are for the appropriate systems in equilibrium. For instance, after the steam is turned off to the enthalpy tank 50, the copper coil 52 is disconnected from the rest of the system and the water bath 58 is stirred until the enthalpy tank has come to thermal equilibrium.

FIG. 4 illustrates a laboratory apparatus and method for developing the empirical data required for measuring downhole steam quality utilizing standard calorimeter techniques with enthalpy tank 50 of FIG. 3 and the flow-through electrode grid structures 10 of FIGS. 1 and 2.

In utilizing this laboratory procedure, the steam quality is measured first with enthalpy tank 50 followed by electrical parameter measurements with electrodes 10 in tube 32.

Plant steam is generated by suitable means, dispensed through a cooler bath having cooling coils 68 used to vary steam quality, then the steam quality is measured first in the enthalpy tank 50 as previously described. Measurements from this enthalpy tank 50 may be fed through lead lines 66 a and b to data logger 44 shown in FIG. 5. After steam quality has been measured in this manner, the steam is then diverted to an experimental vessel 70 containing the pyrex T-tube 32, having flow through electrodes 10 therein. Electrode leads 1, 2 and 3 are fed to the junction box 42.

In every case, the electrode grid system enclosed in the pyrex T-tube 32 is kept at steam temperature by temperature controlled heat tape wrapped around the tube chamber after which the whole chamber is wrapped in insulation. This combination is generally indicated as a heater 72 and is kept at steam temperature by a heater control 74. Various valves V, gauges G and drains D complement the system described. After the electrode chamber in T-tube 32 reaches equilibrium, electrical measurements may be made between each adjacent pair of electrodes, with the data being averaged.

FIG. 5 illustrates a view of a detecting and recording system for the data generated in the laboratory system of FIG. 4.

Temperature measurements are obtained through the thermocouples 22 using a data-logger 44, and electrical parameters are measured through one lead 30 of each thermocouple 22 using an impedance analyzer 46. In measuring the impedance, an operator switches the junction box 42 to scan successive pairs of electrode leads 30 which are input into the junction box 42. Automated data recording is done at 5, 10, 20, 50, 100, 200, 500, 1000, 2000 and 5000 Hertz (Hz) of the parallel capacitance and conductance between each set of electrodes 10 being scanned. At each frequency, a series of measurements is made and averaged, then these data are fed into a computer 48. All data is analyzed by the computer 48 to determine whether computer transfer errors have occurred and corrective measurements are made as needed. Intermediate results may be printed for each frequency, and when measurements have been made over the entire range of frequencies, all accumulated data is stored on magnetic tape for later analysis.

Lead lines 66 a and b entering into data logger 44 serve to transfer data obtained from standard condensing calorimeter techniques as described with respect to FIG. 3. Results from the standard condensing calorimeter technique are used as a basis of comparison to validate the accuracy of the steam quality measurements using the electrical parameters (capacitance) of the flow through electrode grids.

FIG. 6 is a graph showing actual test results correlating steam quality with capacitance between electrodes 1 and 2 at low frequencies (20 Hz) of voltage signals applied therebetween. This proves to be a straight line (linear) relationship, indicating that capacitance measurements using the flow through grid process at low frequencies will yield accurate and easily interpretable steam quality information.

FIG. 7 is a graph showing actual test results correlating steam quality with capacitance between electrodes 1 and 2 at high frequencies (2000 Hz) of voltage signals applied therebetween. The non-linear relationship illustrated makes measurements using the flow-through grid system at high frequencies difficult to predict and may result in erroneous projections of steam quality at the sandface.

Figure 8:
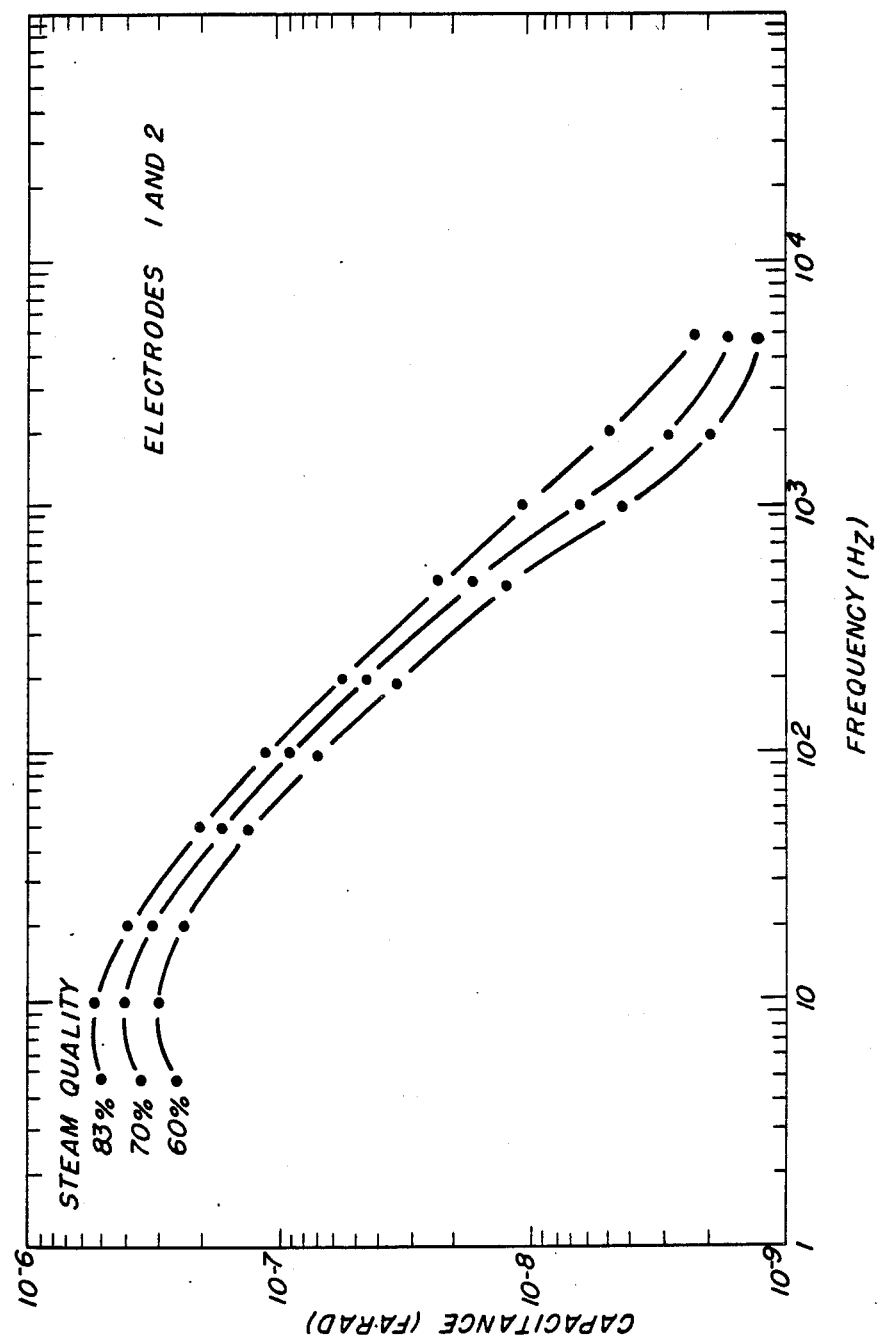
FIG. 8 is a graph illustrating the substantially linear relationship between capacitance and steam quality between a voltage signal frequency range of about 20 to 200 Hz, as determined by the empirical data generated by the system of FIG. 4.

FIG. 8 is a graph illustrating the test results of the laboratory system of FIG. 4 over a wide frequency range of voltage signals applied between electrodes 1 and 2. the results show a substantially linear relationship of steam quality curves between frequency and capacitance in the frequency range from about 20 Hz to 200 Hz. Thus, the test results show that steam quality can be accurately measured as a function of the capacitance between spaced flow-through electrodes over a frequency range of 20 Hz to 200 Hz.

A variation in the geometry of the flow through electrodes previously described could be two concentric cylinders E1,E2 made of a similar wire mesh as in the electrodes 10 illustrated in FIG. 9. Electrodes E1,E2 are mounted such that their center lines are also on the center line of the steam injection string pipe P. Additional information may be obtained from this arrangement such as if any steam has condensed and is on the outer walls of the tubing. This could be measured by obtaining the capacitance M between the outer electrode E1 and the pipe P. The capacitance C between E1 and E2 is measured to determine steam quality.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for measuring the quality of steam flowing through a conduit containing a pair of spaced electrodes comprising the steps of:
   calibrating the system by:
   filling said conduit with steam samples of known qualities;
   applying an AC frequency across said electrodes;
   measuring the capacitance between said electrodes as a function
   of frequency for each steam sample;
   determining a frequency range where measured capacitance is a
   linear function of steam quality; and
   injecting an unknown sample of steam into said conduit;
   applying an alternating voltage at a selected frequency within said
   frequency range to said electrodes;
   measuring the capacitance between said electrodes at said selected frequency; and
   determining steam quality from said capacitance measurement.

2. The method of claim 1 wherein said step of filling said conduit with samples of known steam quality comprises the steps of:
   filling an enthalpy tank with each steam sample;
   calculating steam quality from the measured temperature and enthalpy of the sample;
   diverting said sample from said enthalpy tank to said conduit; and
   maintaining the temperature of the steam in the conduit at the measured temperature in the enthalpy tank.

3. The method for measuring the quality of steam through a conduit according to claim 1, wherein said selected frequency is in a range from about 20 to 200 Hertz.

4. The method for measuring the quality of steam flowing through a conduit according to claim 1 wherein said electrodes include an annular band having a wire mesh supported thereon and extending across the conduit in the path of steam flowing therethrough.

5. The method for measuring the quality of steam through a conduit according to claim 4, wherein said electrodes are stainless steel coated with nickel and gold on top of said nickel.

6. The method for measuring the quality of steam through a conduit according to claim 1, wherein said electrodes may be at least two concentric cylinders positioned in said conduit such that their center axis are on the center axis of said steam being injected.

7. The method for measuring the quality of steam through a conduit according to claim 6, wherein said concentric electrode cylinders have a rectangular wire mesh grid pattern disposed therein.

8. The method of claim 1 wherein said unknown sample is at the injection sandface of a downhole oil well.

* * * * *